United States Patent [19]

Neher et al.

[11] Patent Number: 5,387,720
[45] Date of Patent: Feb. 7, 1995

[54] PROCESS FOR THE PRODUCTION OF ACROLEIN

[75] Inventors: Armin Neher, Brachttal; Thomas Haas, Frankfurt; Dietrich Arntz, Oberursel; Herbert Klenk; Walter Girke, both of Hanau, all of Germany

[73] Assignee: Degussa Aktiengesellschaft, Frankfurt, Germany

[21] Appl. No.: 151,390

[22] Filed: Nov. 12, 1993

[30] Foreign Application Priority Data

Nov. 14, 1992 [DE] Germany ............................. 4238493

[51] Int. Cl.$^6$ ............................................. C07C 45/52
[52] U.S. Cl. ...................... 568/486; 568/449; 568/485
[58] Field of Search ......................... 568/486, 485, 449

[56] References Cited

U.S. PATENT DOCUMENTS

| 1,672,378 | 6/1928 | Freund | 568/486 |
| 2,042,224 | 6/1934 | Groll | 568/486 |
| 2,558,520 | 6/1951 | Hoyt et al. | 568/486 |

FOREIGN PATENT DOCUMENTS 695931 12/1930 France ............................. 568/486

OTHER PUBLICATIONS

Studies in surface science and catalysis, vol. 51, 1989: "New solids acids and bases, their catlytic properties" by K. Tanabe et al., Chapter 1 (pp. 1-3) and chapter 2 (pp. 5-9) were cited on page 7, line 7-10 of the present application.

Organic Syntheses I pp. 15-18 (1964) was cited on page 1, lines 9-10 of the present application.

Ramayya, S., et al., "Acid-catalysed dehyfration of alcohols in supercritical water", Fuel (Oct. 1987) vol. 66, pp. pp. 1364-1371) were cited on page 2, line 20 of the present application.

Chem. Abstracts 110 (6):41924n (Dao, Le H. et al. ACS Symp. Ser., 376 (Pyrolysis Oils Biomass), 328-341 (1988) was cited on page 3, lines 14-16 of the present application.

Chemical Abstracts 101 (4):32598w (Ishikawa Koichi et al., Bunseki Kagaku 32 (10) E 321-E 325) was cited on page 2, lines 5-7 of the present application.

*Primary Examiner*—Werren B. Lone
*Attorney, Agent, or Firm*—Beveridge, DeGrandi, Weilacher & Young

[57] ABSTRACT

A process for the production of acrolein by dehydration of glycerol in the liquid phase or in the gaseous phase, in each case on acidic solid catalysts, is described. Compared with previously known processes, the space-time yield and catalyst service life may be surprisingly increased with higher selectivity by treating a glycerol-water mixture with a glycerol content of 10 to 40 wt. % at 180° to 340° C. (liquid phase) or at 250° to 340° C. (gaseous phase) on a solid catalyst with an $H_o$ value (Hammett acidity function) of less than +2, preferably less than −3.

20 Claims, No Drawings

PROCESS FOR THE PRODUCTION OF ACROLEIN

INTRODUCTION AND BACKGROUND

The present invention relates to a process for the production of acrolein or aqueous acrolein solution by dehydration of glycerol in the liquid or gaseous phase on acidic solid catalysts and to a method of using the aqueous acrolein solution in the production of 1,3-propanediol.

It is known that glycerol may be dehydrated in the presence of acidic substances. According to Organic Synthesis I, 15–18 (1964), acrolein is obtained at a yield of between 33 and 48% of theoretical by treating a mixture of powdered potassium hydrogen sulphate, potassium sulphate and glycerol at 190° to 200° C. The disadvantages of this process are not only the low yield but also the high weight ratio of dehydrating salts to glycerol which is required. This process is therefore unsuitable for the production of acrolein on an industrial scale.

The quantity of acidic catalyst used, such as sulfuric acid, may be kept low if dehydration of glycerol is performed in a homogeneous phase above the critical pressure of water (see S. Ramayya et al. in FUEL (Oct. 1987), Vol. 66, pages 1364–1371). Under the conditions stated in table 4 of that document (34.5 MPa, 350° C., 0.5 molar aqueous glycerol solution), glycerol conversion is 39 to 55%, wherein the main products are acrolein and acetaldehyde in a ratio by weight of approximately 3:1 to 4:1. The considerable technical costs of working in the supercritical range, and the recycling or disposal of the sulfuric acid, make this process unattractive for industrial scale acrolein production.

The formation of acrolein from glycerol in the gaseous phase has also been investigated, for example under destructive gas chromatography conditions (Ishikawa Koichi et al., Bunseki Kagaku 32 (10) E 321-E 325, cited in Chemical Abstracts 101 (4): 32598w). A very dilute glycerol solution (1.5–150 mg/l) is pulsed over a destructive gas chromatography column coated with 10 to 30% $KHSO_4$. The person skilled in the art receives no encouragement from this document to base an industrial acrolein production process on this analytical procedure because glycerol is only used at exceptionally low concentration and the column is practically unaffected by the pulsed reaction.

A process for the production of acrolein from glycerol is known from French patent FR 695,931, wherein glycerol vapors are passed over a fixed bed catalyst at over 300° C. in particular at 400° to 420° C. The catalysts utilized are salts of tribasic acids or mixtures of such salts which may be on a support. According to the examples, pumice coated with 1% lithium phosphate or 1% iron phosphate is used. In this document, the acrolein yield of previously known liquid phase or gaseous phase processes using $KHSO_4$ or $MgSO_4$ is stated to be 20 or 30% respectively, and the yield of the claimed process according to the examples to be 75 or 80%.

The inventors of the present patent application duplicated the process of FR 695,931 and in so doing found that under the tested reaction conditions it was not possible to obtain the indicated yields with either lithium phosphate or iron phosphate. As is shown by the comparative examples, the acrolein yield was only approximately 1 to 3% at 300° C. and 30 to 35% at 400° C.; to a great extent, allyl alcohol, acetaldehyde and propionaldehyde are formed as secondary products. The disadvantage of the process according to FR 695,931 is thus the unsatisfactorily low selectivity of the reaction and consequently the low acrolein yield.

During investigation of model substances for biomass pyrolysis oils, the catalytic treatment of glycerol on H-ZSM5 zeolites at 350° to 500° C. was also investigated (see Dao, Le H. et al. ACS Symp. Ser., 376 (Pyrolysis Oils Biomass), 328–341 (1988), cited in Chem. Abstracts 110 (6): 41924n). Hydrocarbons are formed in only low yield, but reference is made to the formation of acrolein. As was found by the inventors of the present patent application, the dehydration selectivity of H-ZSM5 at, for example, 380° C. in the liquid phase is hardly satisfactory. Furthermore, and this is of decisive importance for an industrial process, under the stated conditions the service life of the catalyst is limited to a few hours.

SUMMARY OF THE INVENTION

An object of the present invention is to provide an industrial process for the production of acrolein or aqueous acrolein solution by dehydration of glycerol in the presence of heterogeneous catalysts. Such a process may be operated with an elevated space-time yield while avoiding the disadvantages of previously known generic processes. Further advantages include a long catalyst service life and high selectivity. The process involves reacting a glycerol-water mixture in either liquid phase or gaseous phase at above 180° C. on a solid catalyst and, optionally, acrolein or aqueous acrolein solution is separated in a known manner by distillation from the reaction mixture. A glycerol-water mixture with a glycerol content of 10 to 40 wt. % is reacted on an acidic solid catalyst, either in the liquid phase at 180° to 340° C. or in the gaseous phase at 250° to 340° C., wherein the $H_o$ value (Hammett acidity function) of the catalyst is less than +2.

Another object relates to a method of using the aqueous acrolein solution directly obtainable from the production process without further processing or purification.

DETAILED DESCRIPTION OF THE INVENTION

It is an essential feature of the present invention that aqueous glycerol solution with a concentration of between 10 and 40 wt. % preferably between 10 and 25 wt. % is passed over the solid dehydration catalyst. Dehydration does indeed still occur if glycerol solutions with a content above 40 wt. % are used; however, as the glycerol concentration rises, both the selectivity of the reaction and the service life of the catalyst are appreciably reduced. Falling selectivity becomes apparent in particular from an increasing proportion of higher-boiling point components. While aqueous glycerol with a concentration below 10 wt. % may indeed be used, economic viability is, however, reduced as concentration falls since the space-time yield is reduced and both the costs for concentrating the acrolein and the energy consumption for vaporizing the water rise.

The production process may be performed in the liquid phase or in the gaseous phase. It is, in principle, possible to use the same solid catalysts in both embodiments; it has, however, proved that certain catalysts are preferably suited for dehydration in the gaseous phase and others preferably for dehydration in the liquid phase.

Reaction in the gaseous phase is particularly preferred because glycerol conversion is practically 100% and the gaseous reaction mixture leaving the catalyst may be directly condensed to obtain an aqueous acrolein solution which additionally contains secondary products which have been formed; this condensate may be directly further processed in many ways. If desired, acrolein, optionally together with a proportion of water, may be recovered from the reaction mixture by distillation or fractional condensation.

When performing the reaction in the liquid phase, it is convenient to dehydrate only to a glycerol conversion of approximately 15 to 25% since selectivity decreases as conversion rises; once the stated conversion is achieved, the acrolein formed is separated from the reaction mixture, either alone or with a proportion of water, in a known manner such as by distillation or $N_2$ stripping. The acrolein may be isolated by condensation or washing with water. The reaction mixture containing glycerol, from which the acrolein has been removed, is returned to the dehydration stage. An advantage of dehydration in the liquid phase over gaseous phase dehydration is lower energy consumption because only the acrolein separated from the reaction mixture together with an accompanying proportion of water need be vaporized.

Dehydration in the gaseous phase preferably proceeds in the temperature range between 270° and 320° C. while liquid phase dehydration preferably proceeds between 250° and 300° C. In the case of liquid phase dehydration, the apparatus is pressurized at least to the pressure necessary to maintain the liquid phase. Conventional apparati known in the art may be utilized.

Increasing the temperature above 340° C. brings about a marked decrease in selectivity. It has surprisingly been found that by limiting the temperature in the dehydration stage to 340° C. and preferably to the above-stated upper limits, the service life of the catalysts is increased to such an extent that they may be continuously operated on an industrial scale.

Homogeneous or multiphase materials with an $H_o$ value of less than $+2$, preferably less than $-3$, and which are substantially insoluble in the reaction medium may be used as acidic solid catalysts. The $H_o$ value corresponds to the Hammett acidity function and may be determined by the well known so-called amine titration using indicators or by adsorption of a gaseous base (see Studies in surface science and catalysis, Vol. 51, 1989: "New solid acids and bases, their catalytic properties" by K. Tanabe et al., chapter 2, in particular pages 5–9). Chapter 1 (pages 1–3) of the above-stated document names many solid acids from which the person skilled in the art may select the appropriate catalyst, optionally after determining the $H_o$ value. Suitable heterogeneous catalysts for dehydration are preferably (i) natural and synthetic siliceous materials, such as in particular mordenite, montmorillonite, and acidic zeolites; (ii) carriers, such as oxidic or siliceous materials, for example $Al_2O_3$ or $TiO_2$, coated with mono-, di-, or polybasic inorganic acids, especially phosphoric acid, or with acid salts of inorganic acids; (iii) oxides and mixed oxides, such as for example gamma-$Al_2O_3$ and ZnO-$Al_2O_3$ mixed oxides or heteropolyacids.

For gaseous phase dehydration, generally catalysts with a $H_o$ value between $+2$ and $-8.2$ are utilized; catalysts with a $H_o$ value between $-3$ and $-8.2$ are preferred; and catalysts with a $H_o$ value between $-5.6$ and $-3$ are most preferred (this includes $H_3PO_4$ on $Al_2O_3$; so-called solid phosphoric acid).

For liquid phase dehydration, catalysts with a $H_o$ value less than $+2$ and even less than $-8.2$ are utilized; catalysts with a $H_o$ value between $-20$ and $-8.2$ are preferred (e.g., zeolite H-ZSM5 type catalysts). While zeolite H-ZSM5 type catalysts are less suitable for gaseous phase dehydration due to their $H_o$ value of less than $-8.2$, they are even preferred for liquid phase dehydration.

The production of catalysts of type (ii) is particularly simple, provided that they are used in gaseous phase dehydration. The support is treated with an aqueous solution of the acid and the treated solid is dried. In the case of liquid phase dehydration, it is recommended to follow drying with conditioning at elevated temperature, for example 0.5 to 2 hours at 400° to 500° C. in order to fix the acid onto the carrier surface.

The production process according to the present invention may be performed in customary plants for gaseous phase or liquid phase reactions on a solid catalyst, as is familiar to the person skilled in the art.

The aqueous acrolein solution obtainable according to the present invention may be directly used, for example for the production of 1,3-propanediol by catalytic hydration to 3-hydroxypropionaldehyde with subsequent catalytic hydrogenation.

A particular advantage of the production process according to the present invention is that aqueous glycerol solutions with a content of 10 to 40 wt. % may be used. So-called crude glycerols may thus be directly used for the production of acrolein or aqueous acrolein solutions; prior concentration and purification of the crude glycerol may therefore be dispensed with.

The simple course of the production process unexpectedly leads to an elevated space-time yield with high selectivity. The particular selection of reaction temperature and glycerol concentration, together with the addition of large quantities of $H_2O$, make it possible to surprisingly achieve a long service life for the heterogeneous catalysts. The invention is further clarified with the following examples and comparative examples.

EXAMPLES 1 to 3

Dehydration in the gaseous phase

Example 1

100 g of 3 mm diameter Rosenthal spheres (alpha-$Al_2O_3$) are mixed with 25 g of a 20 wt. % solution of phosphoric acid for one hour. Excess water is driven off in a rotary evaporator at 80° C. 100 ml of this catalyst ($-5.6 < H_o < -3$) are introduced into a 15 mm diameter steel tube. A 20 wt. % aqueous glycerol solution is pumped at 40 ml/h into a vaporizer heated to 300° C. and this gas stream is directly passed over the catalyst at 300° C. With quantitative conversion of glycerol, a yield of 70.5% of acrolein is obtained in the condensed product stream. Approximately 10% of 1-hydroxyacetone, related to the glycerol, is obtained as a significant secondary product. The catalyst exhibits no loss in activity after 60 hours of operation.

Example 2a and 2b (a) Example 1 was repeated, however with a 40 wt. % aqueous glycerol solution being used. The yield of acrolein was 65%.

(b) Example 1 was repeated, however with an initial acrolein concentration of 10 wt. % being used. The acrolein yield was 75%.

Example 3

Example 1 was repeated, however with a 40 wt. % phosphoric acid being used in production of the catalyst. Yield of acrolein was 69.2%.

EXAMPLE 4

Further processing of 8.6 wt. % aqueous acrolein solution obtained according to example 1 into 1,3- and 1,2-propanediol (PD): The entire acrolein solution was reacted in accordance with DE 40 38 192 (corresponding to U.S. Pat. No. 5,171,898 which is incorporated by reference in its entirety) in an ion exchanger with iminodiacetic acid anchor groups (Lewatit TP 208, Bayer AG) with hydration to 3-hydroxypropionaldehyde. The unreacted acrolein was separated by distillation from the product mixture as a 96% azeotrope with $H_2O$ and combined with the product stream from glycerol dehydration. Under stationary conditions, an initial acrolein concentration of 14.3% was thus obtained, reaction temperature 50° C., LHSV=0.5 $h^{-1}$, conversion=60%, selectivity=85%. The product solution containing 9.6% hydroxypropionaldehyde was hydrogenated in accordance with DE 42 18 282.4 (corresponding to U.S. patent application Ser. No. 08/063,317 which is incorporated by reference in its entirety). A 9.9 wt. % 1,3-propanediol solution was obtained. Apart from the secondary products known in the production of 1,3-propanediol from acrolein, the solution also contained approximately 1 wt. % 1,2-propanediol (1,2 PD). Due to the 25° C. difference in boiling points, it was possible to effectively separate this out by distillation; boiling points of 109° C. for 1,2 PD and 134° C. for 1,3 PD at 50 mbar. The distilled 1,3 PD was of the same quality as 1,3 PD starting from acrolein which was obtained by propene oxidation. Related to the glycerol used, the yield of 1,3 PD was 60%, the yield of 1,2 PD was 10%.

EXAMPLES 5 TO 7

Dehydration in the liquid phase: Glycerol dehydration was continuously performed in a laboratory apparatus with a fixed bed reactor over a moderately long period of time. Conversion and selectivity were determined by analysis of the product solution. The apparatus consists of a container for the glycerol solution, an HPLC pump for conveying the solution, a hot-air oven in which are installed a preheating section together with the reaction tube (160×15 mm internal diameter). Downstream from the reactor, the liquid is cooled to room temperature. The entire apparatus is maintained at a pressure of 70 bar in order to prevent vaporization of the water. The product solution is analyzed at regular intervals of time. See Table 1. The catalysts exhibited no loss in activity after 50 hours of operation.

COMPARATIVE EXAMPLES VB 1 TO VB 4

VB 1: Liquid phase dehydration similar to example 5 but at elevated temperature under the conditions in Table 2. The catalyst was black after 6 hours of operation. Activity had fallen to practically zero.

VB 2: Gaseous phase dehydration with increased glycerol concentration. Example 1 was repeated but with 80 wt. % glycerol being used. The initial yield of acrolein was only 45%; the proportion of high-boiling components rose steeply. After only 4 hours of operation the catalyst was appreciably deactivated.

VB 3: Duplication of the process from FR 695,931. Support material was pellets of pyrogenic silica. The pellets were coated with (a) 1% $Li_3PO_4$ or (b) 1% $FePO_4$. 20 wt. % glycerol was used. Results are shown in Table 3. Significant secondary products included allyl alcohol and acetaldehyde.

VB 4: Gaseous phase dehydration with conditioned catalyst. The catalyst produced in accordance with example 1 was conditioned for 2 hours at 400° C. Dehydration was then performed using this catalyst under otherwise identical conditions as in example 1. The initial yield of acrolein was 36.6%; yield fell to 26.5% after only 4 hours.

VB 5 and 6: Liquid phase dehydration with the catalyst Na-zeolite (VB 5), which has an $H_o$ value in excess of 2.0, led to practically no conversion as may be seen in Table 4. Liquid phase dehydration with gamma-$Al_2O_3$ as catalyst (VB 6), which has an $H_o$ value greater than 1.5 and less than 4.0 ($1.5 < H_o < 4.0$), gives completely insufficient selectivity, even when the initial glycerol concentration is very low as seen in Table 4.

Further variations and modifications of the foregoing will be apparent to those skilled in the art and such variations and modifications are attended to be encompassed by the claims that are appended hereto.

German Priority Application P 42 38 492.3, filed on Nov. 14, 1992, and German Priority Application P 42 38 493.1, filed on Nov. 14, 1992, are relied on and incorporated by reference. U.S. Pat. Nos. 5,015,789 and 5,171,898 and U.S. patent application Ser. Nos. 07/981,324 (filed on Nov. 24, 1992), 08/063,317 (filed on May 19, 1993), and 07/948,718 (filed on Sep. 24, 1992) are incorporated by reference in their entirety.

TABLE 1

| Example yno. | Catalyst | Temp. (°C.) | Pressure (bar) | LHSV ($h^{-1}$) | $C_{Gly.O}$ (wt. %) | $C_{AC}$ (wt. %) | U (%) | S (%) | $H_o$ |
| --- | --- | --- | --- | --- | --- | --- | --- | --- | --- |
| 5 | Zeolite HZSM-5 modulus 60 | 250 | 70 | 2 | 10 | 0.74 | 16 | 75 | $<-8.2$ |
| 6 | Zeolite HZSM-5 modulus 28 | 300 | 70 | 2 | 10 | 0.8 | 19 | 71 | $<-8.2$ |
| 7 | Mordenite | 250 | 70 | 2 | 10 | 0.35 | 8 | 71 | $<-8.2$ |

$C_{Gly.O}$ = glycerol feed concentration
$C_{AC}$ = acrolein feed concentration
U = conversion
S = selectivity
LHSV = liquid hourly space velocity

TABLE 2

| Catalyst | Temp. (°C.) | Pressure (bar) | LHSV (h$^{-1}$) | $C_{Gly.O}$ (wt. %) | $C_{AC}$ (wt. %) | U (%) | S (%) |
| --- | --- | --- | --- | --- | --- | --- | --- |
| Zeolite HZSM-5 modulus 60 | 380 | 180 | 5 | 10 | 0.75 | 22 | 56 |

TABLE 3

| Catalyst | Temperature | Yield of acrolein |
| --- | --- | --- |
| (a) Li$_3$PO$_4$ | 400° C. | 31.5% |
|  | 300° C. | 1.3% |
| (b) FePO$_4$ | 400° C. | 35.7% |
|  | 300° C. | 2.3% |

TABLE 4

| No. | Catalyst | Temp. (°C.) | Pressure (bar) | LHSV (h$^{-1}$) | $C_{Gly.O}$ (wt. %) | $C_{AC}$ (wt. %) | U (%) | S (%) |
| --- | --- | --- | --- | --- | --- | --- | --- | --- |
| VB 5 | Na-ZSM5 | 250 | 70 | 2 | 10 | — | <1 | — |
| VB 6 | gamma Al$_2$O$_3$ | 350 | 70 | 2 | 1 | 0.04 | 22 | 30 |

What is claimed:

1. A process for the production of acrolein or aqueous acrolein solution by dehydration of glycerol, said process comprising reacting a glycerol-water mixture with a glycerol content of 10 to 40 wt. % in either liquid phase at 180° to 340° C. or gaseous phase at 250° to 340° C. on an acidic solid catalyst and optionally separating acrolein or aqueous acrolein solution, wherein the H$_o$ value (Hammett acidity function) of said catalyst is less than +2.

2. The process according to claim 1, wherein said gaseous phase is at 270° to 320° C.

3. The process according to claim 1, wherein said liquid phase is at 250° to 300° C. and at the pressure necessary to maintain said liquid phase.

4. The process according to claim 1, wherein said glycerol content is 10 to 25 wt. %.

5. The process according to claim 1, wherein in said gaseous phase said acidic solid catalyst has a H$_o$ value is less than +2 to −8.2.

6. The process according to claim 1, wherein in said gaseous phase said acidic solid catalyst has a H$_o$ value between −3 and −8.2.

7. The process according to claim 1, wherein in said gaseous phase said acidic solid catalyst has a H$_o$ value between −3 and −5.6.

8. The process according to claim 7, wherein in said gaseous phase said acidic solid catalyst is H$_3$PO$_4$ on Al$_2$O$_3$.

9. The process according to claim 1, wherein in said liquid phase said acidic solid catalyst has a H$_o$ value between −20 and −8.2.

10. The process according to claim 9, wherein in said liquid phase said acidic solid catalyst is a H-ZSM5 or H-Y catalyst.

11. The process according to claim 1, wherein said acidic solid catalyst is a mordenite, montmorillonite or acidic zeolite.

12. The process according to claim 1, wherein said acidic solid catalyst is a oxidic or siliceous carrier coated with mono-, di-, or polybasic inorganic acids or with acid salts of inorganic acids.

13. The process according to claim 12, wherein said carrier is Al$_2$O$_3$ or TiO$_2$ coated with phosphoric acid.

14. The process according to claim 1, wherein said acidic solid catalyst is an oxide, mixed oxide or heteropolyacid.

15. The process according to claim 14, wherein said acidic solid catalyst is gamma-Al$_2$O$_3$ or ZnO-Al$_2$O$_3$.

16. The process according to claim 1, wherein said reaction is continued to a glycerol conversion of 8 to 25%, the acrolein formed is separated from the reaction mixture alone or with a proportion of the water by stripping and the acrolein-free reaction mixture is returned to the dehydration stage.

17. The process according to claim 1, wherein said separating is by distillation.

18. A method of using the acrolein or aqueous acrolein solution produced by method according to claim 1 to form 1,3-propanediol, comprising catalytically hydrating said acrolein or aqueous acrolein solution to 3-hydroxypropionaldehyde and catalytically hydrogenating said 3-hydroxypropionaldehyde to 1,3-propanediol.

19. A process for the production of acrolein or aqueous acrolein solution by dehydration of glycerol, said process comprising reacting a glycerol-water mixture with a glycerol content of 10 to 40 wt. % in either (a) liquid phase at 180° to 340° C. on an acidic solid catalyst, wherein the H$_o$ value (Hammett acidity function) of said catalyst is less than +2, until a glycerol conversion of 8 to 25% is achieved, the acrolein formed is separated from the reaction mixture alone or with a proportion of the water by stripping and the acrolein-free reaction mixture is returned to the dehydration stage, or (b) gaseous phase at 250° to 340° C. on an acidic solid catalyst, wherein the H$_o$ value (Hammett acidity function) of said catalyst is less than +2 to −8.2;

and optionally separating acrolein or aqueous acrolein from the reaction mixture.

20. The process according to claim 1, said process consisting essentially of reacting a glycerol-water mixture with a glycerol content of 10 to 40 wt. % in either (a) liquid phase at 180° to 340° C. and optionally at the pressure necessary to maintain said liquid phase or (b) gaseous phase at 250° to 340° C., on an acidic solid catalyst and optionally separating acrolein or aqueous acrolein solution, wherein the H$_o$ value (Hammett acidity function) of said catalyst is less than +2; and optionally continuing said reaction to obtain a glycerol conversion of 15 to 25% separating the acrolein formed from the reaction mixture alone or with a proportion of the water by stripping and returning the acrolein-free reaction mixture to the dehydration stage.

* * * * *